(12) United States Patent
Heinz et al.

(10) Patent No.: US 7,056,900 B2
(45) Date of Patent: Jun. 6, 2006

(54) DISACCHARIDE DERIVATIVES FOR TREATING HYPERGLYCAEMIA

(75) Inventors: Fritz Heinz, Hannover (DE); Sabine Hertel, Langenhagen (DE); Markwart Kunz, Worms (DE); Manfred Vogel, Neuleiningen (DE)

(73) Assignee: Sudzucker Aktiengesellschaft Mannheim Ochsenfurt (DE)

( * ) Notice: Subject to any disclaimer, the term of this patent is extended or adjusted under 35 U.S.C. 154(b) by 0 days.

(21) Appl. No.: 10/192,459

(22) Filed: Jul. 9, 2002

(65) Prior Publication Data

US 2003/0087841 A1 May 8, 2003

Related U.S. Application Data

(62) Division of application No. 09/530,519, filed as application No. PCT/EP98/05857 on Sep. 16, 1998, now Pat. No. 6,677,317.

(30) Foreign Application Priority Data

Oct. 31, 1997  (DE) ................. 197 48 195

(51) Int. Cl.
*A61K 31/7016* (2006.01)
*C07H 5/04* (2006.01)
*C07H 5/06* (2006.01)

(52) U.S. Cl. .................. 514/53; 514/25; 514/866; 536/187; 536/53; 536/123.1; 424/94.5

(58) Field of Classification Search ............... 536/18.7, 536/53, 123.1; 514/53, 25, 866; 424/94.5
See application file for complete search history.

(56) References Cited

FOREIGN PATENT DOCUMENTS

| DE | 2830424 | | 1/1980 |
| DE | 4307388 | | 9/1994 |
| DE | 4310032 | | 9/1994 |
| DE | 19542303 | | 5/1997 |
| EP | 0560284 | | 9/1993 |
| EP | 0599646 | | 6/1994 |
| EP | 599646 | * | 6/1994 |
| EP | 599646 A2 | * | 6/1994 |
| GB | 2011397 | | 7/1979 |
| GB | 2011397 A | * | 7/1979 |

OTHER PUBLICATIONS

Pietsch et al., "Regioselective synthesis of new sucrose derivatives via 3-ketosucrose." Carbohydrate Research, 254, No. 17, pp. 183-194, 1994.*

Pietsch et al., "Regioselective synthesis of new sucrose derivatives via 3-ketosucrose." Carbohydrate Research, 254, No. 17, pp. 183-194, 1994.*

M. Kunz, et al., "Katalytische Oxidation Von Isomaltulose", *Chemie. Ingenieur. Technik*, Bd. 67, Nr. 7, Jul. 1995, pp. 836-842.

M. Pietsch, et al., "Regioselective Synthesis of New Sucrose Derivatives Via 3-ketosucrose", *Carbohydrate Research*, Bd. 254, No. 17, Feb. 1994, pp. 183-194.

* cited by examiner

*Primary Examiner*—James O. Wilson
*Assistant Examiner*—Devesh Khare
(74) *Attorney, Agent, or Firm*—Ostrolenk, Faber, Gerb & Soffen, LLP

(57) ABSTRACT

The invention relates to the use of the disaccharide derivatives 3'-aminosucrose, sucrose-C6-acid and palatinose-C6'-acid and/or of an amide or alkyl ester thereof for the prevention or treatment of hyperglycemias.

8 Claims, No Drawings

DISACCHARIDE DERIVATIVES FOR TREATING HYPERGLYCAEMIA

CROSS-REFERENCE TO RELATED APPLICATIONS

This is a division of application Ser. No. 09/530,519, filed Jun. 6, 2000, now U.S. Pat. No. 6,677,317 which is based upon PCT International Application No. PCT/EP98/05857, filed Sep. 16, 1998, claiming priority of German Application No. 197 48 195.7, filed Oct. 31, 1997.

DESCRIPTION

The invention relates to drug compositions and food compositions for treating hyperglycemias in the human or animal body and process for inhibiting α-glucosidases.

The breakdown of carbohydrates in the human or animal body requires the presence of α-glucosidases, in particular sucrases and maltases. Inhibitors of these two enzymes prove to be advantageous, in particular if an increase in the blood sugar level after meals is to be prevented. EP 0 560 284 A1 discloses α-glucosidase inhibitors which do not have harmful effects on the patient and in addition are taken by the patient only to a small extent. This publication discloses the use of various pentoses and hexoses such as L-arabinose, L-fucose, L-xylose, D-ribose etc. to inhibit the α-glucosidase activity in a homogenate comprising maltase and sucrase.

GB 2 011 397 A1 discloses that sugars produced by Streptomyces (Actinomyces A 2396) show a glycosidase-inhibiting action. The sugars disclosed in GB 2 011 397 A1 are oligomeric compounds which are at least trisaccharides.

The technical problem underlying the present invention is to provide a drug composition or food composition comprising an inhibitor for the enzyme activity of sucrase and maltase enzyme activities with simultaneously high physical tolerance.

The technical problem underlying the present invention is solved by providing a drug composition or food composition which comprises disaccharide derivatives, in particular oxidized disaccharides or their derivatives such as amides or alkyl esters of the oxidized disaccharides or amino derivatives of disaccharides and if appropriate a pharmaceutically acceptable excipient. In a particularly preferred embodiment of the invention, the oxidized disaccharide derivatives provided according to the invention are methyl and ethyl esters of the oxidized disaccharide. In a further preferred embodiment, the oxidized disaccharide derivatives provided according to the invention are their amides having the general structure R'—CO—NHR, where R'—CO is the oxidized disaccharide and R=H or R=$C_nH_{(2n+1)}$ where n=0–5. In particular, the technical problem is solved by such a drug composition or food composition which comprises a monocarboxylic acid of sucrose, in particular the C6'-sucrose monocarboxylic acid, called sucrose-C6-acid hereinafter, and/or an oxidized palatinose (isomaltulose), in particular the palatinose-C6'-acid. The problem is also solved by a food composition or drug composition which in a preferred embodiment comprises an amino sucrose, in particular 3'-aminosucrose.

It has surprisingly been found that the enzyme activities of sucrase and maltase were particularly strongly inhibited by the above-mentioned disaccharide derivatives to be used according to the invention, in particular 3'-aminosucrose, and the oxidized disaccharides or their above-mentioned alkyl esters or amides, in particular the sucrose-C6-acid and the palatinose-C6'-acid. The compounds used according to the invention are therefore suitable for reducing the blood sugar level and accordingly for the prevention and treatment of hyperglycemias.

The invention also relates to a drug composition comprising as active constituent the above-mentioned disaccharide derivatives to be used according to the invention, in particular 3'-aminosucrose, and/or oxidized disaccharides or their above-mentioned alkyl esters or amides, in particular sucrose-C6-acid and/or palatinose-C6'-acid, and a pharmaceutically acceptable excipient or additives for reducing an increased blood sugar level or for the treatment and prevention of hyperglycemias of the animal and human body. The drug composition according to the invention can accordingly be used not only prophylactically but also therapeutically.

The invention also relates to a food composition or what is termed a "functional food", comprising the disaccharide derivatives used according to the invention and if appropriate food-compatible additives which can be used, for example, for the prevention or accompanying treatment of increased blood sugar level and hyperglycemias.

The above-described disaccharide derivatives used according to the invention have the advantage that they have a strongly inhibiting action on the sucrase and maltase activities. In particular, the disaccharide derivatives used according to the invention are therefore suitable for preparing a drug and/or food for the prevention or treatment of hyperglycemias.

The invention also relates to the use of the above-described disaccharide derivatives used according to the invention for preparing the above-mentioned compositions.

Pharmaceutically acceptable and/or food-acceptable excipients or additives which can be used in combination with the disaccharide derivatives used according to the invention are, for example, binders, preservatives, stabilizers, release agents and lubricants, sweeteners, colorings and flavorings or the like.

The compositions of the invention can be present as tablets, powders, pills, compressed preparations or solutions and can be administered, for example, orally or intraperitoneally. The dosage is preferably from 0.2 to 90% by weight.

In food compositions of the invention it is preferably provided to use at least 0.2% by weight, preferably from 2 to 50% by weight (based on the total weight of carbohydrates present in the food) of the inventive disaccharide derivatives.

The invention therefore also relates to a process for inhibiting α-glucosidases, in particular maltase and sucrase activities, in which the disaccharide derivatives to be used according to the invention, in particular 3'-aminosucrose, the oxidized disaccharides or their alkyl esters or amides, in particular sucrose-C6-acid and/or palatinose-C6'-acid are added to an aqueous solution comprising the glucoamylase/maltase enzyme complex and/or the sucrase/isomaltase enzyme complex and an effective inhibition of the sucrase activity and/or maltases activity is achieved.

The invention is described in more detail with reference to an exemplary embodiment.

EXAMPLE

Determination of the enzyme activities of sucrase, maltase and isomaltase in the enzyme complexes sucrase/isomaltase (SI) and glucoamylase/maltase (GM)

A) The activity of the SI enzyme complex was studied using three different substrates, that is to say sucrose, maltose and isomaltose.

The isomaltase activity was studied using the substrate isomaltose.

The maltase activity was studied using the substrate maltose.

The preparation of 3'-aminosucrose is described in Pietsch, M. et al., Carbohydrate research 254 (1994), 183 to 194.

The preparation of palatinose-C6'-acid is described in Kunz et al., Chem.-Ing.-Tech. 67 (1995), 836–842.

The preparation of sucrose-C6-acid is described in EP 0 651 734 B1.

Triethanolamine hydrochloride (TRA), adenosine 5'-triphosphate (ATP), nicotinamide adenine dinucleotide (NAD), hexokinase (HK) and glucose-6-phosphate dehydrogenase (G6PDH) were obtained from Boehringer/Mannheim and magnesium chloride hexahydrate from Merck.

Sucrase/isomaltase (SI) and glucoamylase/maltase (GM) were isolated by papain digestion from hog small intestine mucosa and enriched by ammoniumsulfate precipitation. The enzymes were separated into isolated sucrase/isomaltase (SI) and glucoamylase/maltase (GM) via an ion exchanger (DEAE cellulose), and a following fine fractionation using gel filtration on a Superdex 200 column from Pharmacia.

B) In the methods described hereinafter for determining the enzyme activity of sucrase/isomaltase and glucoamylase/maltase under the influence of the substances tested, the amount of glucose or fructose released was determined as measured parameter. This took place in an enzymatic optical test using hexokinase (HK) and glucose-6-phosphate dehydrogenase (G6PDH) as a coupled detection system (Beutler, H.-O.; in: Methods of Enzymatic Analysis; Bergmeyer, H. U.; Bergmeyer, J.; Graβl, M. (editors); 3rd edition; Vol. VI, 2–10). The measurement was made at 37° C. and a pH of 7.0.

The table below reports the composition of the assays necessary for the individual tests. In individual tests, the semimicro assay was used, but this was reduced in some cases to a micro assay.

TABLE 1

Composition of the individual assays.

| | Semimicro assay | | Concentration | Micro assay | |
|---|---|---|---|---|---|
| Substance[1] | | Volume | in the assay | Substance[1] | Volume |
| Substrate solution (1.6 × X mM) | | 0.620 mL | X mmol/L, varying within a series of measurements | Substrate solution (1.67 × X mM) | 0.210 mL |
| TRA (100 mM), pH 7 | | 0.100 mL | 100 mmol/L | TRA (100 mM), pH 7 | 0.035 mL |
| Mixture of: (i) ATP (16.2 mM) (ii) NAD+ (4.4 mM) (iii) MgCl2 (40 mM) | | 0.250 mL | 4.05 mmol/L 1.1 mmol/L 10 mmol/L | Mixture of: (i) ATP (18.9 mM) (ii) NAD+ (5.1 mM) (iii) MgCl2 (46.7 mM) | 0.075 mL |
| Warm assay to 37° C. within 15 min | | | | | |
| Mixture of: (i) HK (70 U/mL) (ii) G6P-DH (500 U/mL) | | 0.010 mL | 0.7 U/mL 5.0 U/mL | Mixture of: (i) HK (24.5 U/mL) (ii) G6P-DH (175 U/mL) | 0.010 mL |
| Allow glucose present in the substrate to react to completion; incubate for a further 5 min for this | | | | | |
| Enzyme (5 U/mL maltase activity) 1.000 mL | | 0.020 mL | 0.1 U/mL | Enzyme (1.75 U/mL maltase activity) 0.350 mL | 0.020 mL |

[1]All solutions were made up in TRA-buffer (100 mM), pH 7.

C) Before the inhibitor strengths were determined, for each enzyme-substrate combination basic kinetics were established in which not only the Michaelis-Menten constant ($K_M$ [mmol/l]) but also the maximum velocity ($V_{max}$ [μmol/mL min]) were determined. For the enzyme/substrate combination SI/sucrose, a substrate concentration of from 1.24 to 124 mmol/L was used, for the enzyme/substrate combination SI/maltose a substrate concentration of from 0.62 to 24.8 mmol/L was used, for the enzyme/substrate combination SI/isomaltose a substrate concentration of from 3.6 to 57.6 mmol/L was used and for the enzyme/substrate combination GM/maltose a substrate concentration of from 0.31 to 12.4 mmol/L was used in the assay.

TABLE 2

Kinetic constants of SI for the substrate sucrose, maltose and isomaltose and of GM for maltose as substrate

| Enzyme/substrate combination | $K_M$ [mmol/L] | $V_{max}$ [U/mL] |
|---|---|---|
| SI/sucrose | 58.8 ± 11.4 | 7.7 ± 1.7 |
| SI/maltose | 11.2 ± 2.6 | 5.9 ± 0.4 |
| SI/isomaltose | 73.9 ± 6.8 | 3.07 ± 0.18 |
| GM/maltose | 4.2 ± 1.0 | 4.8 ± 0.7 |

Table 2 shows the $K_M$ and $V_{max}$ values of sucrase/isomaltase (SI) with the substrates sucrose, maltose and isomaltose and of glucoamylase/maltase (GM) with the substrate maltose (the values reported are the means of all basic kinetics carried out, the $V_{max}$ value is based on an enzyme solution having a maltase activity of 5 U/mL, determined at substrate saturation).

D) A study was first made as to what extent the inventive disaccharide derivatives and comparison substances, that is to say sucrose and maltose, were cleaved by SI or by GM during incubation for 24 hours.

TABLE 3

Incubation assay

| Substance | Volume | Concentration in the assay |
|---|---|---|
| Sample | 0.230 mL | between 15.5 and 18.5 mmol/L |
| Warm assays to 37° C. in the course of 15 min | | |
| SI or GM 1.25 U/mL maltase activity ⇒ Sample dilution | 0.020 mL | 0.1 U/mL maltase activity ⇒ between 14.3 and 17 mmol/L |
| 0.250 mL | | |
| Withdraw an aliquot of 0.220 mL from incubated assay solutions after 24 hours. Stop reaction by heating to 95° C. (2 min) Store samples in ice bath or freeze at −20° C. | | |

The results are shown in Table 4.

TABLE 4

Cleavage of the disaccharide derivatives on incubation (24 hours) with SI or GM compared with cleavage of the natural substrate sucrose and maltose

| Substance | cleavage product detected | SI conversion rate [%] | GM conversion rate [%] |
|---|---|---|---|
| Sucrose | glucose fructose | 85 87 | no incubation carried out |

TABLE 4-continued

Cleavage of the disaccharide derivatives on incubation (24 hours) with SI or GM compared with cleavage of the natural substrate sucrose and maltose

| Substance | cleavage product detected | SI conversion rate [%] | GM conversion rate [%] |
|---|---|---|---|
| Maltose | glucose | 100 | 95.7 |
| 3'-A-Suc | fructose | 0 | 0 |
| Suc-C6S | glucose | 2 | 0 |
| Pal-C6'-S | fructose | 0.4 | 0.1 |

(3'-A-Suc: 3'-aminosucrose, suc-C6S: sucrose-C6-acid, pal-C6'S: palatinose-C6'-acid)

E) For each enzyme-substrate combination, inhibitor kinetics were then carried out using 3'-aminosucrose, sucrose-C6-acid and palatinose-C6'-acid. The level of the inhibitor concentrations used depended on the strength of the resulting inhibition. For each of the enzyme-substrate combinations, 3 to 4 sets of kinetics at different inhibitor concentrations were established. The inhibitor constants $K_i$ and $K_{ii}$ were, unless stated otherwise, determined from secondary Lineweaver-Burk plots.

In the tables below K means competitive inhibition, NK means noncompetitive inhibition and UK means uncompetitive inhibition.

TABLE 5

Inhibition of SI/sucrose and SI/maltose by 3'-aminosucrose. Comparison (i) of inhibition in two different procedures and (ii) of the $K_i$ values resulting from a Henderson evaluation or Dixon evaluation.

| | without preincubation Type $K_i$ [× $10^{-6}$ M] | | | with preincubation Type $K_i$ [× $10^{-6}$ M] | |
|---|---|---|---|---|---|
| SI/sucrose | NK | Henderson: | 5.0 | K Henderson: | 6.3 |
| | | Dixon: | 5.2 | Dixon: | 6.5 |
| SI/maltose | NK | Henderson: | 5.2 | K Henderson: | 4.6 |
| | | Dixon: | 5.4 | Dixon: | 4.6 |

TABLE 6

Inhibition of the SI-catalyzed hydrolysis of sucrose, maltose and isomaltose by carboxyl derivatives of sucrose and palatinose

| Carboxyl derivative | SI/sucrose | | | SI/maltose | | | SI/isomaltose | | |
|---|---|---|---|---|---|---|---|---|---|
| | Type | $K_i$ [mM] | $K_{ii}$ [mM] | Type | $K_i$ [mM] | $K_{ii}$ [mM] | Type | $K_i$ [mM] | $K_{ii}$ [mM] |
| Suc-C6S | NK | 9 | 9 | NK | 43 | 5 | NK | 73 | 3 |
| Pal-C6'S | NK | 7 | 8 | NK | 16 | 31 | K | 20 | — |

TABLE 7

Inhibition of the GM-catalyzed hydrolysis of maltose by 3'-aminosucrose

| Amino derivative | Type | $K_i$ [mM] | $K_{ii}$ [mM] |
|---|---|---|---|
| 3'A-Suc | NK | 1 | 17 |

TABLE 8

Inhibition of the GM-catalyzed hydrolysis of maltose by carboxyl derivatives of sucrose and palatinose

| Carboxyl derivative | Type | $K_i$ [mM] | $K_{ii}$ [mM] |
|---|---|---|---|
| Suc-C6S | UK | — | 4 |
| Pal-C6'S | K | 20 | — |

It is shown that 3'-aminosucrose inhibits the enzyme complexes SI and GM to a high percentage even at very low concentrations (Tables 4 and 6). In the case of the combination SI/sucrose and SI/maltose, even at an inhibitor concentration of 1 mmol/L, enzymatic activity was no longer measurable. At a concentration of 5 µmol/mL, the sucrose hydrolysis was about 30% inhibited and the maltose hydrolysis about 50% inhibited.

It is also shown that the sucrose and palatinose carboxyl derivatives used according to the invention not only significantly inhibit SI but also GM (Tables 6 and 8).

F) The tables below give overviews of the inhibition strengths with which the disaccharide derivatives used according to the invention act on the enzyme/substrate combinations studied.

TABLE 9

Inhibition of SI by carboxyl derivatives of sucrose and palatinose: $K_M/K_i$ values and ratio formation of competitive and uncompetitive inhibition components

| Carboxyl derivative | SI/sucrose | | | SI/maltose | | | SI/isomaltose | | |
|---|---|---|---|---|---|---|---|---|---|
| | Type | $K_M/K_i$ | $K_i/K_{1i}$ | Type | $K_M/K_i$ | $K_i/K_{ii}$ | Type | $K_M/K_i$ | $K_i/K_{1i}$ |
| Suc-C6S | NK | 6.2 | 1 | NK | 0.26 | 9 | NK | 1 | 21.6 |
| Pal-C6'S | NK | 8.4 | 0.88 | NK | 0.7 | 0.54 | K | 3.7 | — |

TABLE 10

Inhibition of GM by carboxyl derivatives of sucrose and palatinose: $K_M/K_i$ values and ratio formation of competitive and uncompetitive inhibition components

| Carboxyl derivative | Type | $K_M/K_i$ | $K_i/K_{ii}$ |
|---|---|---|---|
| Suc-C6S | UK | — | — |
| Pal-C6'S | K | 0.22 | — |

TABLE 11

Inhibition of SI by 3'-aminosucrose. $K_M/K_i$ values and ratio formation of competitive and uncompetitive inhibition components

| Amino derivative | SI/sucrose | | | SI/maltose | | | SI/isomaltose | | |
|---|---|---|---|---|---|---|---|---|---|
| | Type | $K_M/K_1$ | $K_i/K_{ii}$ | Type | $K_M/K_1$ | $K_i/K_{i1}$ | Type | $K_M/K_i$ | $K_i/K_{ii}$ |
| 3'A-Suc | NK | 11530 | 1 | NK | 2113 | 1 | K | 8.2 | — |

TABLE 12

Inhibition of GM by 3'-aminosucrose. $K_M/K_i$ values and ratio formation of competitive and uncompetitive inhibition components

| Amino derivative | Type | $K_M/K_i$ | $K_i/K_{ii}$ |
|---|---|---|---|
| 3'A-Suc | NK | 3.1 | 0.06 |

The strength of an enzyme inhibition may be read off from the inhibition constants $K_i$ and $K_{ii}$. The $K_M/K_i$ value permits statements to be made as to the ratio of the affinity between enzyme and natural substrate to the affinity between enzyme and inhibitor:

Very strong inhibitors have a $K_M/K_i$ ratio >2.

Strong inhibitors have a $K_M/K_i$ ratio between 1 and 2.

Weak inhibitors have a $K_M/K_i$ ratio <1.

Substances without any inhibitor function have a $K_M/K_i$ ratio very much less than 1.

It can be seen from the tables that sucrose-C6-acid and palatinose-C6'-acid are strong to very strong inhibitors of the enzyme/substrate combinations SI/sucrose and SI/isomaltose and also have inhibitory action for the enzyme/substrate combination SI/maltose. Palatinose-C6'-acid also has inhibitory action for the enzyme/substrate combination GM/maltose. 3'-aminosucrose is a strong to very strong inhibitor of all the enzyme/substrate combinations studied.

The invention claimed is:

1. A drug composition comprising an active ingredient and a carrier in which said active ingredient is an amide or alkyl ester of an oxidized disaccharide and wherein the oxidized disaccharide is selected from the group consisting of monocarboxylic acids of sucrose and oxidized palatinose.

2. A drug composition according to claim 1 in which the amide of an oxidized disaccharide has the general formula R'—CO—NHR in which R'—CO is the oxidized disaccharide and R is hydrogen or $C_{1-5}$ alkyl.

3. A drug composition according to claim 1 in which the alkyl ester is a methyl or ethyl ester of the oxidized disaccharide.

4. A composition comprising a food and an additive in which the additive is an amide or alkyl ester of an oxidized disaccharide and wherein the oxidized disaccharide is selected from the group consisting of monocarboxylic acids of sucrose and oxidized palatinose.

5. A composition according to claim 4 in which the amide of an oxidized disaccharide has the general formula R'—CO—NHR in which R'—CO is the oxidized disaccharide and R is hydrogen or $C_{1-5}$ alkyl.

6. A composition according to claim 4 in which the alkyl ester is a methyl or ethyl ester of an oxidized disaccharide.

7. The drug composition of claim 1 wherein the monocarboxylic acid of sucrose is sucrose-C6-acid.

8. The drug composition of claim 1 wherein the oxidized palatinose is palatinose-C6'-acid.

* * * * *